(12) United States Patent
Dieker et al.

(10) Patent No.: US 9,376,504 B2
(45) Date of Patent: *Jun. 28, 2016

(54) HYBRID SEPARATION

(71) Applicant: ICM, Inc., Colwich, KS (US)

(72) Inventors: Kurt A. Dieker, Wichita, KS (US); Charles C. Gallop, Gower, MO (US); Scott D. Kohl, Wichita, KS (US); Keith Tjaden, Clearwater, KS (US); Justin McMillen, Wichita, KS (US)

(73) Assignee: ICM, Inc., Colwich, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/028,020

(22) Filed: Sep. 16, 2013

(65) Prior Publication Data

US 2014/0080183 A1   Mar. 20, 2014

Related U.S. Application Data

(60) Provisional application No. 61/701,834, filed on Sep. 17, 2012.

(51) Int. Cl.
| | |
|---|---|
| *A23L 7/10* | (2016.01) |
| *C12P 7/10* | (2006.01) |
| *C08B 30/04* | (2006.01) |
| *C12P 19/02* | (2006.01) |
| *C12P 19/14* | (2006.01) |
| *C12M 1/00* | (2006.01) |

(52) U.S. Cl.
CPC .............. *C08B 30/042* (2013.01); *C12P 7/10* (2013.01); *C12P 19/02* (2013.01); *C12P 19/14* (2013.01); *C12M 21/12* (2013.01); *C12M 43/02* (2013.01); *C12M 45/04* (2013.01); *C12M 47/10* (2013.01); *Y02E 50/16* (2013.01); *Y02E 50/17* (2013.01)

(58) Field of Classification Search
CPC .................................. C08B 30/042; C12P 7/10
See application file for complete search history.

(56) References Cited

U.S. PATENT DOCUMENTS

| | | |
|---|---|---|
| 2,132,250 A | 10/1938 | Wagner |
| 4,255,518 A | 3/1981 | Muller et al. |
| 4,495,207 A | 1/1985 | Christianson et al. |
| 5,344,576 A | 9/1994 | Carr et al. |
| 5,460,717 A | 10/1995 | Grimwood et al. |
| 7,727,726 B2 | 6/2010 | Cates et al. |
| 2005/0255190 A1 | 11/2005 | Mehra et al. |
| 2008/0220125 A1 | 9/2008 | Abbas et al. |

(Continued)

FOREIGN PATENT DOCUMENTS

| | | |
|---|---|---|
| EP | 2471585 A1 | 7/2012 |
| WO | WO-2014/043627 A1 | 3/2014 |

OTHER PUBLICATIONS

"International Application U.S. Appl. No. PCT/US2013/059956, International Search Report mailed Dec. 17, 2013", 4 pgs.

(Continued)

*Primary Examiner* — Karen Cochrane Carlson
*Assistant Examiner* — Jennifer M.H. Tichy
(74) *Attorney, Agent, or Firm* — Schwegman Lundberg & Woessner, P.A.

(57) ABSTRACT

This disclosure describes techniques for using a single feedstock of barley to produce a fermented product and a method for filtering a large-particles stream from a liquid stream containing small particles of a process stream using a series of mechanical separation devices to increase yield.

11 Claims, 11 Drawing Sheets

(56) References Cited

U.S. PATENT DOCUMENTS

| | | |
|---|---|---|
| 2008/0279983 A1 | 11/2008 | Lohrmann et al. |
| 2009/0005539 A1 | 1/2009 | Scheimann et al. |
| 2009/0259018 A1 | 10/2009 | Barrows et al. |
| 2009/0269817 A1 | 10/2009 | Lantero |
| 2010/0260918 A1 | 10/2010 | Wang et al. |
| 2011/0151516 A1* | 6/2011 | Van Der Heide ... C08B 37/0003 435/72 |
| 2012/0244590 A1 | 9/2012 | Lee |

OTHER PUBLICATIONS

"International Application Serial No. PCT/US2013/059956, Written Opinion mailed Dec. 17, 2013", 8 pgs.

Wahjudi, J., et al., "Quick Fiber Process: Effect of Mash Temperature, Dry Solids, and Residual Germ on Fiber Yield and Purity", Cereal Chem. 77(5):640-644, (2000), 640-644.

Canadian Application No. 2,827,146, Office Action mailed Mar. 25, 2015, 3 pgs.

Canadian Application No. 2,827,146, Office Action mailed May 14, 2014, 2 pgs.

Canadian Application No. 2,827,146, Response filed Apr. 1, 2015 to Examination Report mailed Mar. 25, 2015, 5 pgs.

Canadian Application No. 2,827,146, Response filed Nov. 10, 2014 to Examination Report mailed May 14, 2014, 12 pgs.

International Application Serial No. PCT/US2013/059956, International Preliminary Report on Patentability mailed Mar. 26, 2015, 10 pgs.

Notice of Allowance from Canadian Patent Office, Application No. 2,827,146, filing date Sep. 16, 2013, Fiber Separation Technology.

* cited by examiner

HYBRID SEPARATION

CROSS REFERENCE TO RELATED APPLICATION

This application claims the benefit of priority under 35 U.S.C. §119(e) of U.S. Provisional Patent Application Ser. No. 61/701,834, filed on Sep. 17, 2012, the contents of which is hereby incorporated by reference in its entirety.

TECHNICAL FIELD

The subject matter of this disclosure pertains to using a single feedstock of grain to produce a fermentation product, using a combination of two different types of feedstock grain to produce a fermentation product, treating components from a single feedstock or a combination of feedstocks by using a hybrid separation process to improve oil recovery and to increase yield, and adding different types of enzymes at various stages of a process to increase yield in a production facility.

BACKGROUND

Increased production is a key component to increasing a supply of transportation fuels, increasing chemical applications, food applications, feed applications, and the like that are derived from renewable plant resources. Typically, a dry grind process or a wet mill process may use corn as feedstock for producing alcohol, ethanol, butanol, and the like in a production facility. The dry and wet processes differ in complexities, which affect capital costs, preparation of feedstock, types of co-products produced, and different types of primary products produced.

The dry grind process offers several advantages over the wet mill process. For instance, the dry grind process provides lower capital costs and lower operating costs. However, the dry grind process only produces alcohol, distillers' grain, carbon dioxide, and oil.

Wet mills are able to separate grain so components may be efficiently recovered and purified. Wet mills produce more high-valued products, such as food products, alcohol, gluten meal, gluten feed, starch, oil, and syrup. However, wet mills cost substantially more to build and have higher operating costs than dry grind mills. Wet mills are also typically much larger in size than dry grind mills.

There have been attempts to use the dry grind process or the wet mill process with other types of grain (i.e., not corn) as feedstock to produce alcohol. However, these processes may require significant modifications to the existing production facilities due to the abrasive nature of hull from some grains, varying carbohydrate concentration, micronutrients, and high viscosity of certain grain mashes.

Accordingly, there is a need for converting other types of grain as feedstock for various applications in a more cost-efficient manner. Accordingly, there is also a need for separating solids in a cost efficient manner, recovering and purifying components, without significantly affecting quality of the product or co-products, and improving oil recovery and yield.

SUMMARY

This disclosure describes a process for using a single feedstock of barley to produce a fermented product. The process includes removing hulls from the barley and grinding barley berries and liquefying the barley berries with an alpha-amylase and water to create a slurry. The process also includes saccharifying the slurry by adding a glucoamylase to a mash and fermenting the mash with a microorganism to produce the fermentation product.

This disclosure also describes methods for improving yield in a production facility by filtering a large-particles stream from a slurry containing small particles and dissolved materials based on a series of mechanical separation devices. The method further includes adding water to the large-particles stream to create a lower-solids stream and heating the lower-solids stream in a tank. The method further includes using at least one or more mechanical separation devices that further separates the large-particles stream from the liquid stream containing small particles and dissolved components.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other aspects and advantages of the claimed subject matter will be apparent from the following Detailed Description of the embodiments and the accompanying figures.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures do not limit the claimed subject matter to specific embodiments described herein.

DETAILED DESCRIPTION

Overview

Figure 1:
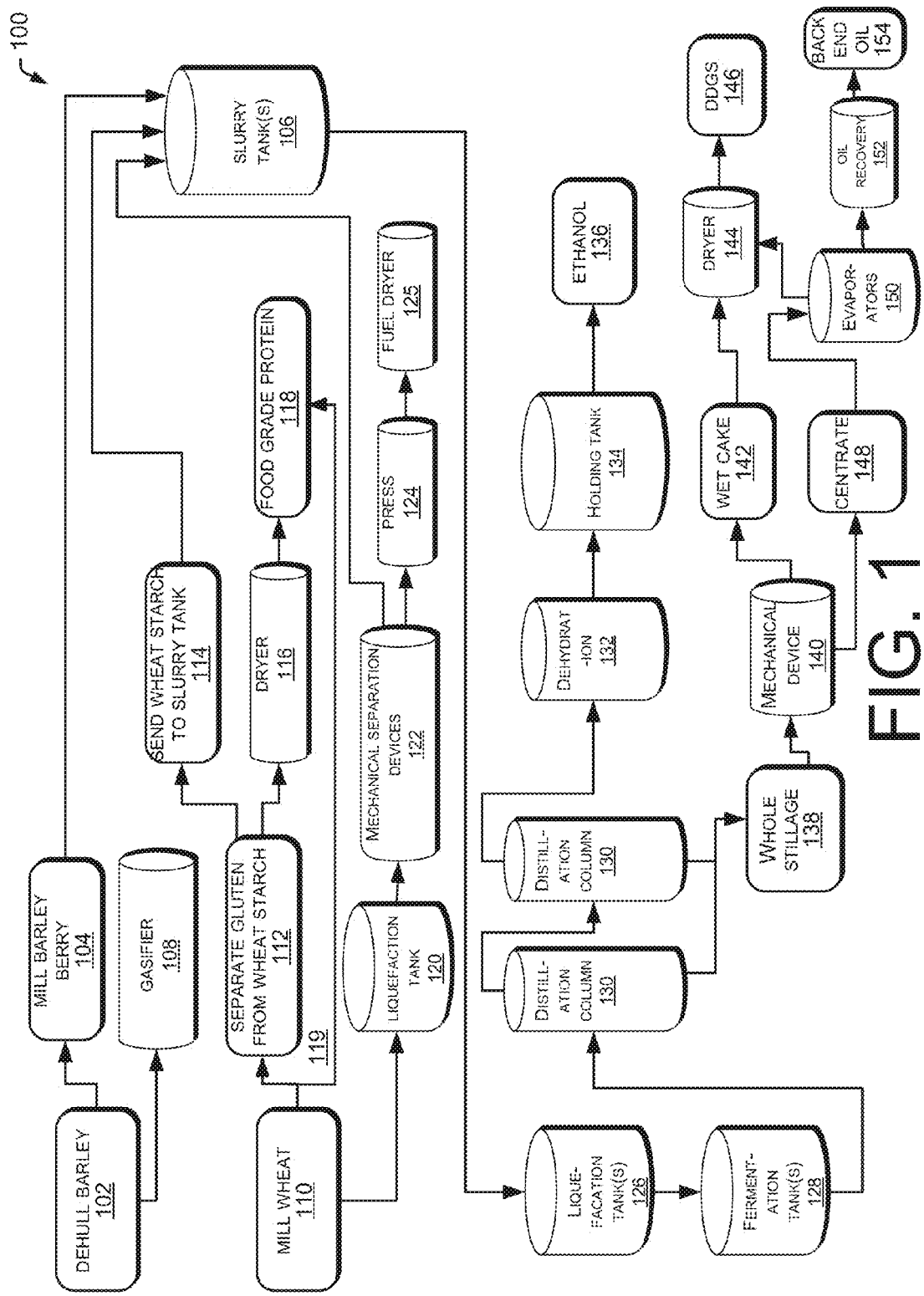
FIG. 1 illustrates an example process using a combined feedstock of barley and wheat to produce a fermentation product.

The Detailed Description explains embodiments of the subject matter and the various features and advantageous details more fully with reference to non-limiting embodiments and examples that are described and/or illustrated in the accompanying figures and detailed in the following attached description. Descriptions of well-known components and processing techniques may be omitted so as to not unnecessarily obscure the embodiments of the subject matter. The examples used herein are intended merely to facilitate an understanding of ways in which the subject matter may be practiced and to further enable those of skill in the art to practice the embodiments of the subject matter. Accordingly, the examples, the embodiments, and the figures herein should not be construed as limiting the scope of the subject matter.

This disclosure describes techniques to use a single feedstock or to use a combination of two different feedstocks to produce product in a production process. Variables that affect profitability of producing alcohol, include type of grain (i.e., feedstock), availability of the grain, and price of the grain. For instance, this technique describes how to produce a product by using a single feedstock of barley, a combined feedstock of barley and wheat, or a combined feedstock of other types of grain. However, other types of a single feedstock of grain or other types of combination of feedstocks of grain may also be used to produce product. For instance, the grain may include but is not limited to, barley, wheat, oats, rye, triticale, sweet potatoes, cassava, corn, milo, sorghum grain, and the like.

The techniques for the single feedstock include dehulling the barley, grinding the barley berry, sending the feedstock to a slurry tank, adding enzymes to the slurry, converting the slurry to mash, and fermenting the mash to produce product. The techniques for the combined feedstock stream include grinding the barley berry, milling wheat to produce food grade protein from wheat starch, combining the wheat starch and the ground barley berry in a slurry, adding enzymes and water to the slurry, converting the slurry to mash, and fermenting the mash to produce product.

This disclosure also describes techniques to implement a Hybrid Separation (HS) process that improves converting starch to a fermentation product by using a pre-separation method before fermentation. The HS process may be used in any order (after fermentation) or any type of production facility. The HS process removes nonfermentables size gradients that are twice as large before a fermentation process, which in turn increases the concentration of alcohol produced per fermentation tank, increases speed of fermentation, and decreases a likelihood of fermentations not occurring. However, the HS process also recovers the nonfermentables to use in a co-product in the process.

The HS process uses a combination of different methods. The HS process mills and separates components of feedstock by using different types of shearing and separation devices. The HS process then combines the feedstock into slurry. In an embodiment, the HS process uses a counter-flow wash on the combined feedstock stream received from a slurry tank by using mechanical separation devices. In another embodiment, the HS process may wash the starch out of the fiber by using the HS process using a series of mechanical separation devices in concurrent wash process.

One of the mechanical separation devices may be a paddle-screen separation device, which has low cost and high practical throughput. In embodiments, the HS process uses a single or a series of mechanical separation devices to separate a large suspended solids stream from a liquid with fine suspended solids, including but not limited to, one to ten devices. In an embodiment, the HS process uses a single mechanical separation step to separate a large suspended solids stream from a liquid with fine suspended solids. In other embodiments, the HF process uses a series of two or more mechanical separation steps. In another embodiment, the HS process uses a series of four mechanical separation steps. In an embodiment, the HS process adds water to each stage of the counter-flow washing in the series. In another embodiment, the HS process adds clean water to each stage of the concurrent washing in the series. This raises water activity for better starch to sugar conversion. Raising the water activity also increases oil leaching rate and completeness from germ moieties.

The HS process cooks the water and the large suspended solids stream at a temperature range often used in the production process. For instance, a slurry temperature may be about 55° C. to about 60° C. (about 328 K to about 333 K) that is below a starch gelatinization point to get good wetting of the grain. The cook temperature for the HS process ranges from about 70° C. to about 130° C. (about 343 K to about 403 K). The HS process does not increase the solids content, does not negatively affect the viscosity of the material, and/or does not negatively affect the yield from fermentation process. Thus, there are no significant energy penalties, and no known degrading of the quality of the co-products, such as Dried Distillers Grain with Solubles (DDGS).

The HS process further washes the stream by using wash water (i.e., received from a mechanical separation device, clean, and the like) and removes additional amounts of starch from the fiber by going through another mechanical separation device. This helps to remove excess water since a liquid stream containing small particles produced during the wash process is directed back to the start of the slurry process. The HS process may use two or more mechanical separation devices to further wash and separate the large-particles from the small particles, to clean the starch from the fiber, and to recover a portion of the nonfermentables. Thus, the HS process allows higher starch to alcohol conversion efficiencies without altering the water balance in the production process.

Other advantages of the HS process include using no special enzymes or creating a very fine grind. The HS process also avoids low temperatures that increase risk of bacterial contamination and does not create high fines for back-end recovery of a cold cook or a fine-grind of a dry grain. Thus, there are significant advantages to using the HS process. The HS process may be used in conjunction with any type of single feedstock or a combined feedstock to produce alcohol.

This disclosure also describes techniques of improving the yield of product by adding different types of enzymes to various stages of the production process. The enzymes include but are not limited to, beta-glucanase, beta-glucosidase, endoglucanase, or cellobiohydrolase. The enzymes do not need a low temperature, so risk of bacterial contamination is avoided. Beta-glucanase has a high degree of stability that makes it durable to pH extremes. These enzymes have been found to be particularly effective with the grains of barley, as it attacks beta-glucan fiber to liberate smaller fragments (i.e., a cell wall modification). The rate of modification is determined by contents of the cell walls of beta-glucan.

While aspects of described techniques can be implemented in any number of different environments, and/or configurations, implementations are described in the context of the following example environment.

Illustrative Environments

FIGS. 1-10 include flow diagrams showing example processes. The processes may be performed using different environments and devices. The equipment should not be construed as necessarily order dependent in their performance. Any number of the described processes or equipments may be combined in any order to implement the method, or an alternate method. Moreover, it is also possible for one or more of the provided steps or pieces of equipment to be omitted.

FIG. 1 illustrates an example of a process 100 using a series of operations found in a wet mill and a dry mill process of a production facility. For instance, the process 100 operates in a continuous manner. However, the process may be performed in a batch process or a combination of continuous and batch processes.

The process 100 may receive feedstock of a grain that includes but is not limited to, barley, wheat, oats, rye, triticale, sweet potatoes, cassava, corn, milo, sorghum grain, sugar cane, and the like. The feedstock may include an individual type, a combined feedstock of two types, or any combination or blend of the above. The feedstock may include one to ten different types combined in various percentage ranges. The production facility processes the feedstock to convert the grain into different co-products that may include germ to be extracted for oil, food grade protein feed for high fiber animal feed, food grade protein meal for high protein animal feed, and starch-based and fermentation-based products such as ethanol, syrup, food, and industrial starch. Other types of applications include but are not limited to, producing chemicals, chemicals for use in other applications, and the like.

For brevity purposes, the process of using a combined stream will be described with reference to FIG. 1. As mentioned, barley, corn, wheat, triticale, or rye may be used as a single feedstock, which is not shown. The process for the single feedstock of barley or corn will be similar to the process described in FIG. 1. However, the portions pertaining to wheat for milling wheat, would not be applicable.

The amount of starch in barley may be about 50 to 64% and amount of beta-glucan about 4% and the amount of starch in wheat may be about 60%. By using a combined feedstock with the techniques described reduces an amount of feedstock bushels needed to yield the same amount of alcohol. In an embodiment, the process 100 uses barley and wheat in a combined feedstock along with the techniques described to reduce the amount of barley bushels needed from 47.7 million bushels per year to 41.2 million bushels per year and the amount of wheat bushels needed from 14.7 million bushels per year to 15.2 million bushels per year for an approximate yield of 115 million gallons of denatured alcohol per year (MMgpy).

The process 100 initially dehulls the barley 102 into berry and hulls, and further grinds the barley berry 104 into a meal or a powder using a roller mill. The berry is defined as a naked berry. In another embodiment, a hammer mill may be used to grind the barley berry. Devices to dehull the barley include but are not limited to, an abrasive dehulling device, hammer mill, roller mill, disc mill, ball mill, pin mill, a shaker table, an aspiration system, and the like.

In an embodiment, the process 100 may add moisture to the barley berry before milling to optimize milling efficiency. The water softens the endosperm, which is the starchy portion of the barley. In another embodiment, the process 100 may not add moisture to the barley berry prior to milling. The endosperm will be separated out from the other components, the bran, which contains fiber, and the like.

Devices to perform the milling of the barley include hammer mill, roller mill, disc mill, ball mill, pin mill, and the like. In an embodiment, the process 100 uses a roller mill having at least a pair of rolls or wheels to grind the barley. The barley goes into the top of the roller mill, passes between two or more rolls or wheels and is crushed in the process. One roll is fixed in position while the other roll may be moved further away or closer towards the stationary roll. The roll surfaces may be grooved to help in shearing and disintegration of the barley. The rolls may be about 9 to 12 inches (23 to 30.5 cm) in diameter, with a ratio of length to diameter may be about 4:1.

Milling helps prepare the barley to work efficiently with water and enzymes to be discussed later. The process 100 sends the milled barley berry to a slurry tank 106. The slurry tank 106 will be discussed further in details below.

Returning to 102, as discussed above, the process 100 dehulls the barley into berries and hulls. The process 100 then sends the hulls to a gasifier 108 to make energy for use in the production facility. Alternately, the hulls could be converted to cellulosic ethanol.

At 110, the process 100 separates the wheat to be about 72% yield of endosperm and about 28% yield of wheat middlings (i.e., MIDDS). The process 100 separates the components of the endosperm, such as separating the food grade protein from wheat starch 112, which is about 86% of starch. The process 100 sends the wheat starch to the slurry tank 114. Next, the process 100 sends the food grade protein, which is the protein composite, to a dryer 116 (e.g., ring dryer) and then packages the food grade protein 118 to be sold as animal feed. Another portion shown as 119, from the endosperm portion may be sent directly to a blending station for product exiting from dryer 116 to make the food grade protein 118.

The middlings contains about 28% starch and a total solids content of about 87%. The middlings go through a liquefaction tank 120 to be mixed with water to form a slurry. This watering facilitates separation of the various components in the middlings. The process 100 sends the water and middlings, which include fine particles of wheat bran, wheat germ, wheat flour, and offal from the liquefaction tank 120 to mechanical separation devices 122.

The one or more mechanical separation devices 122 separate the larger particles in the stream from the smaller particles in the stream. The mechanical separation device 122 includes but is not limited to a paddle screen, a pressure screen device, DSM screen, and the like. The paddle screen includes openings that are sized to permit water, starch, and food grade protein to flow through the screen while retaining the larger particles, such as fiber.

After a single separation process using a mechanical separation device, the process 100 may further wash the fiber or large particles stream to remove additional amounts of starch and/or food grade protein. The process 100 may include but is not limited to, one to ten multiple washing stages using several mechanical separation devices 122. As mentioned, the process 100 adds water to the large particles stream to further wash and to help remove the starch from the fiber.

After the mechanical separation devices 122, the starch portion goes to the slurry tank 106. Another portion, the fiber portion of the middlings, may go through a press 124 to remove moisture content. After going through the press 124, the fiber portion of the middlings has a total solids content of about 39%. The fiber portion is then sent to the dryer to be processed as filler for pet food or as human food or as boiler fuel.

Returning to the slurry tanks 106, the process 100 adds water and enzymes to the combined materials to create a slurry in a tank (i.e., slurry tank). In an example, enzymes that may be added include but are not limited to, alpha-amylase and beta-glucanase. The alpha-amylase breaks starch polymer into short sections. The amount of alpha-amylase may range from 0.02 to 0.06 w/w % of incoming grain, depending on specific activity of enzyme formulations. Meanwhile, the beta-glucanase breaks down beta-linked glucose polymers that are associated with grains. The beta-glucanase breaks down $(1\rightarrow3)$, $(1\rightarrow4)$-$\beta$-glucan, a polysaccharide made of glucose sub-units. The β-glucan break down may occur randomly of the molecule. Beta-glucanase that may be used include but are not limited to, β-glucanase, an enzyme that breaks down (1→3), (1→4)-β-glucans and β-1,6-glucanase, an enzyme that breaks down β-1,6-glucans. The amount of beta-glucanase added may range from 0.005 to 0.06 w/w % (depending on specific activity of enzyme formulations) of incoming grain and added at temperature ranges from about 45° C. to about 75° C. (about 318 K to about 348 K).

Beta-glucanase has been found to be particularly effective with the grains of barley, as it attacks (1→3), (1→4)-β-glucan fiber to liberate smaller fragments (i.e., a cell wall modification). The rate of modification is determined by contents of the cell walls of beta-glucan. Beta-glucanase hydrolyzes beta D-glucan component and breaks down the beta-linked glucose polymers that are often associated with barley or wheat.

The pH of the slurry may be adjusted to about 5.0 to 6.0. Furthermore, the temperature may be maintained between 60 to 100° C. (333 to 373K) in the slurry tank 106 and a residence time of about 30 to 60 minutes to convert the insoluble starch in the slurry to soluble starch. The slurry may have dissolved solids content of about 15 to 45%. Other items in the slurry tank 106 may include sugars, protein, fiber, starch, germ, grit, oil and salts, and the like as is commonly present on raw incoming grain from agricultral production. There may be one or more slurry tanks 106 in the production facility.

In embodiments, the slurry may or may not be heated in the slurry tank to reduce viscosity of the milled grain. Some processes may include an optional jet cooking process.

When the jet cooking process is used, jet cookers (not shown) will cook the slurry. Jet cooking may occur at elevated temperatures and pressures. For example, jet cooking may be performed at a temperature of about 100 to 150° C. (about 212 to 302° F.) and at an absolute pressure of about 1.0 to 6.0 kg/cm$^2$ (about 15 to 85 lbs/in$^2$) for about five minutes. Jet cooking is one method used to gelatinize the starch.

At 126, the process 100 converts the slurry to mash in liquefaction tank(s). This occurs at about 80 to 95° C. (353 to 368 K) to hydrolyze the gelatinized starch into maltodextrins and oligosaccharides to produce a liquefied mash. Here, the mash stream has about 18 to 45% total solids content. The mash may have suspended solids content that includes fiber, germ, grit, and the like.

The process 100 may add another enzyme, such as glucoamylase in the liquefaction tanks 126 to break down the dextrins into simple sugars. The glucoamylase breaks the short sections into individual glucose molecules. The glucoamylase may be added at about 60° C. (333 K) before fermentation, known as saccharification or at start of a fermentation process. The process 100 adjusts the pH to 5.0 or lower. In an embodiment, saccharification and fermentation may also occur simultaneously.

At 128, the process 100 adds microorganism and other enzymes, beta-glucosidase and amyloglucosidase to the mash in the fermentation tank(s). A common strain of microorganism, such as *Saccharomyces cerevisiae* may be used to convert the simple sugars (i.e., maltose and glucose) into alcohol (with solids and liquids), $CO_2$, and heat.

The beta-glucosidase is a glucosidase enzyme that acts upon β-1-3 and β-1-4 bonds that link two glucose molecules or glucose-substituted molecules. By cleaving the β-1-3 and β-1-4 linkage, beta-glucosidase may generate D-glucose. In other words, the beta-glucosidase acts on these molecules by releasing a sugar molecule. In particular, the beta-glucosidase has specificity for a variety of beta-D-glycoside substrates. The process 100 adds the beta-glucosidase at a temperature range of about 40° C. to about 28° C. (104 to 82° F., about 313 to about 301 K) and in an amount ranging from 0.001 to 0.09% w/w % of incoming grain (dosage based on formulated enzyme activity).

The combination of beta-glucanase and beta-glucosidase are able to hydrolyze the (1→3), (1→4)-β-glucan components of barley. For instance, barley contains about 56% starch and 4% beta-glucan. These two enzymes work together to help make beta-glucan appear more like glucose to yeast. Thus, the effective, fermentable concentration is that as if the raw material had about 60% starch. Therefore, the yield increases by about 7 to 8%, changing the need from 47.7 million bushels of barley per year to 41.2 million bushels of barley per year and the amount of wheat bushels needed from 14.7 million bushels per year to 15.2 million bushels per year for a 115 million gallons of denatured alcohol per year (MMgpy).

This residence time in the fermentation tank(s) may be about 50 to about 60 hours. However, variables such as microorganism strain being used, rate of enzyme addition, temperature for fermentation, targeted alcohol concentration, and the like affect fermentation time.

The process 100 creates the alcohol, solids, and liquids through fermentation. Once completed, the mash is commonly referred to as beer, which may contain about 13 to 16% alcohol, plus soluble and insoluble solids from the grain components, microorganism metabolites, and microorganism bodies. The microorganism may be recycled in a microorganism recycling step, which is an option.

Turning to 130, the process 100 distills the beer to separate the alcohol from the non-fermentable components, solids, and the liquids by using one or more distillation columns. The beer is pumped through a series of two or more distillation columns 130 and boiled to vaporize the alcohol. The alcohol vapor is condensed in the distillation columns 130 and liquid alcohol exits through a top portion of the distillation columns 130 at about 88 to 93% purity, which is about 190 proof. Factors affecting distillation 130 include column size, energy flux, product flow rate, and ethanol concentration.

At 132, the process 100 removes moisture from the 190 proof alcohol by going through dehydration, such as a molecular sieve device. The molecular sieve device includes one or more dehydration column(s) packed with molecular sieves to yield a product of nearly 100% alcohol, which is 200 proof alcohol.

The process 100 adds a denaturant to the alcohol prior to or in the holding tank 134. Thus, the alcohol is not meant for drinking but is to be used for motor fuel purposes. At 136, an example product that may be produced is motor fuel grade ethanol, to be used as fuel or fuel additive for motor fuel purposes.

The water rich product remaining from the distillation column 130 is commonly referred to as "whole stillage" 138. The components in the whole stillage 138 may include suspended grain solids, dissolved materials, and water. For instance, this material includes fat, protein, fiber, and minerals. Whole stillage 138 falls to the bottom of the distillation columns 130 and passes through a mechanical device 140. The mechanical device 140 separates the whole stillage 138 to produce "wet cake" (i.e., insoluble solids) at 142 and centrate (i.e., liquids) at 148. The mechanical device may include a centrifuge, decanter, or any other type of separation device. The mechanical device may increase solids content from about 10 to about 15% up to about 25 to about 44% solids. There may be one or more mechanical devices.

The wet cake 142, primarily solids, may be referred to as Wet Distillers Grain (WDG). This includes, but is not limited to, protein, fiber, fat, and liquids. Some of the wet cake is transferred to one or more dryer(s) 144 to remove moisture.

This drying produces Dried Distillers Grain (DDG), which may be stored in tanks to be used as livestock feed (not shown).

Returning to 148, the process 100 produces centrate. Centrate 148 is mostly the liquids left over from whole stillage 138. The centrate 148 is sent to the evaporators 150 to boil away water, producing thin stillage. The process 100 may further boil away moisture from the thin stilage, leaving a thick syrup (i.e., 25 to 45% dry solids) that contains soluble solids (dissolved), fine suspended solids (generally less than 50 um) and buoyant suspended solids from fermentation. The thick syrup from the centrate 148 may be sent to the dryer 144 with the wet cake 142 (i.e., WDG) to produce DDGS 146.

In an embodiment, the process 100 sends the liquids to oil recovery 152, which removes oil from the syrup to recover oil. The process 100 may send materials from oil recovery 152 back to the evaporators 150. The process 100 produces a product of back-end oil 154.

Illustrative Milling Processes

Figure 2:
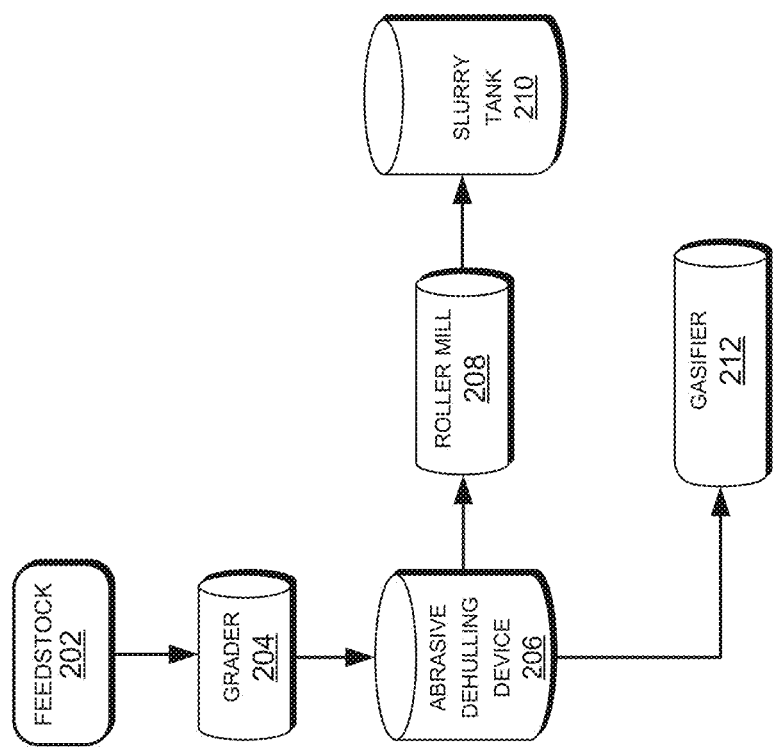
FIG. 2 illustrates an example of dehulling barley in a process.

FIG. 2 illustrates an example process 200 of milling and separating barley feedstock in a HS process. This process 200 uses hulled barley as an example but hulless or naked barley may be used in the process. Other types of feedstock grain may also be used in this process.

The process 200 receives barley as feedstock 202 in railcars or trucks. The process 200 cleans the barley feedstock 202 by going through a grader 204. The grader 204 may be an oscillatory screening device that separates items found with the feedstock 202. The separation occurs based on particle sizes. For instance, the process 200 screens large-size particles that may include trash or form materials, medium-size particles that include barley, and small-size particles that may include sand, broken grains, and the like.

The process 200 sends the medium-size particles, the barley, to an abrasive dehulling device 206. The abrasive dehulling device 206 may be any type of mechanical device to separate components of the barley. For instance, the abrasive dehulling device 206 may include a rotor/disk, emery stations, and perforated screen.

The abrasive dehulling service 206 separates the inedible, fibrous, outer hulls from the components of the barley. The components of the barley (i.e., bran, germ, barley berries) goes to a milling device. The milling device includes but is not limited to roller mill, hammer mill, disc mill, and the like. For instance, the process 200 sends the components to a bin hopper or a roll feeder (not shown) and to the roller mill 208.

The roller mill 208 includes at least a pair of rolls or wheels to grind the barley. The barley goes into a top of the roller mill, passes between two or more rolls or wheels and is crushed in the process. One roll may be fixed in position while the other roll may be moved further or closer towards the stationary roll. The roll surfaces may be grooved to help in shearing and disintegration of the barley. The rolls may be about 9 to 12 inches (23 to 30.5 cm) in diameter, with a ratio of length to diameter may be about 4:1.

In another embodiment, the two rolls may rotate at the same speed causing compression force to be used on the barley. In another embodiment, the two rolls may operate at different speeds to increase compression and shear stress. The roller mill may include screens that are located along the bottom of the rolls to allow particles of a certain size to pass through the screen. The screen openings may be $6/64$ to $9/64$ inches (2.38 mm to 3.56 mm). In an embodiment, the screen openings may be $7/64$ inches, or about 2.78 mm to create particles that are sized less than 45 microns to 2-3 mm.

The process 200 may include an aspirator (not shown), which is optional. This reduces the amount of bran by removing the bran cut. The process 200 sends the barley berries to the slurry tank 210 that is part of a production facility.

Returning to the abrasive dehulling device 206, the process 200 sends the hulls to a gasifier combustion system 212 to make energy for use in the production facility.

In another embodiment, a hammer mill is used to grind the barley. After grinding in the hammer mill, the process then sends the ground material to a slurry tank.

Figure 3:
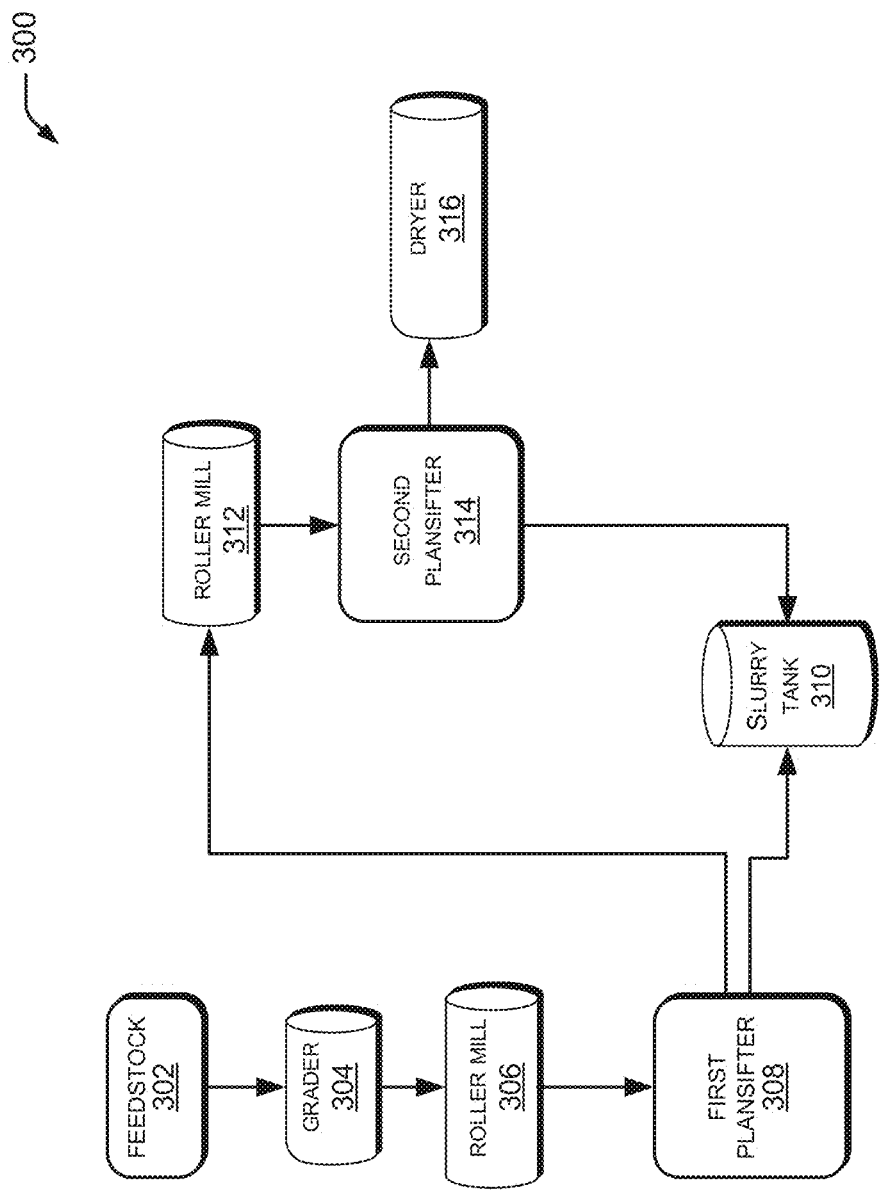
FIG. 3 illustrates an example of milling wheat in a process.

FIG. 3 illustrates an example of milling wheat in a process 300. This process 300 uses wheat as an example but other types of feedstock grain may also be used in this process.

The process 300 receives wheat as feedstock 302 in railcars or trucks. The process 300 cleans the wheat feedstock 302 by going through a grader 304. The grader 304 may be an oscillatory screening device that separates items found with the feedstock 302. The separation occurs based on particle sizes. For instance, the process 300 screens large-size particles that may include trash or form materials, medium-size particles that may include wheat, and small-size particles that may include sand, broken grains, and the like.

The process 300 sends the wheat feedstock to a bin hopper or a roll feeder (not shown) and to a milling device. The milling device includes but is not limited to roller mill, hammer mill, disc mill, pin mill, ball mill, and the like.

The roller mill 306 performs similar functions and has similar designs to the description for the roller mill 208 described with reference to FIG. 2. In an embodiment, the two rolls may rotate at the same speed causing compression force to be used on the wheat. In another embodiment, the two rolls may operate at different speeds to increase compression and shear stress. The roller mill 306 may include screens that are located along the bottom of the rolls to allow particles of a certain size to pass through the screen. The screen openings may be sized $6/64$ to $9/64$ inches. In an embodiment, the screen openings may be $7/64$ inches, or about 2.78 mm to create particles that are sized less than 45 microns to 2-3 mm.

The process 300 sends the ground wheat to a first plansifter 308. The first plansifter 308 sorts different products based on using a sifter with multiple sieves per compartment. The first plansifter 308 separates the components of the wheat, such as the endosperm and fiber/middlings. The process 300 then sends the endosperm through another roller mill 312 and through a second plansifter 314. Here, the second plansifter 314 separates the gluten from the wheat starch. The process 300 further sends the gluten to be dried by a dryer 316. Returning to the second plansifter 314, the process 300 sends the wheat starch to a slurry tank 310 for further processing.

Illustrative Hybrid Separation Processes

Figure 4:
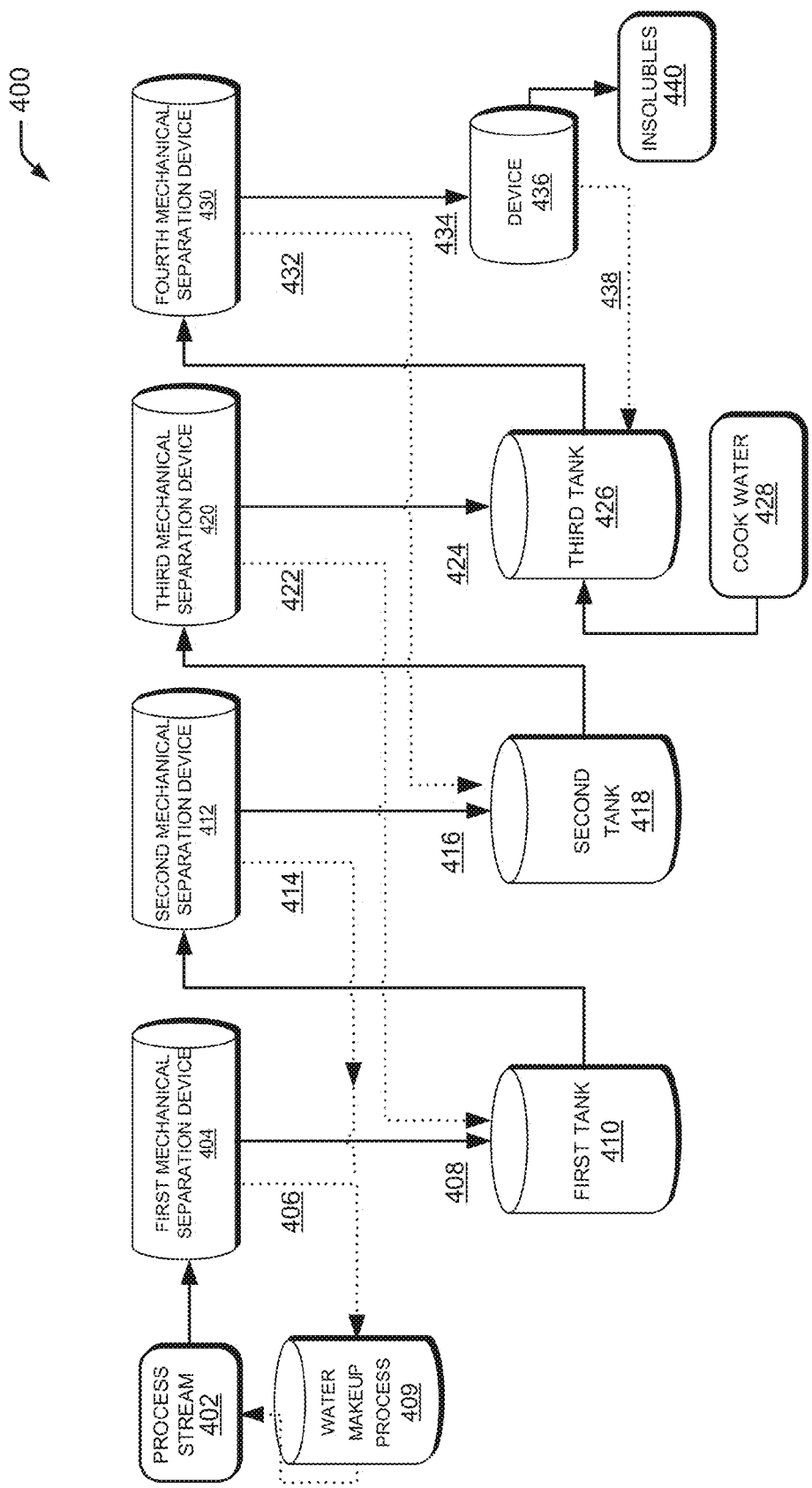
FIG. 4 illustrates an example of a hybrid separation process using a counter-flow wash process.

FIG. 4 illustrates an example of the HS process 400 using a counter-flow wash process. For illustrative purposes, the liquids and fine suspended particles streams are identified by dotted lines to indicate being sent to a tank. These examples illustrate streams that may be sent from the mechanical separation devices and streams received into the tanks from the different mechanical separation devices. However, the liquids and fine suspended particle streams may be sent to water make up process, a receiving tank, a slurry tank, a liquefaction tank, a remix tank, and the like, while any streams may be received into the tanks from any of the mechanical separation devices. The terms, such as large-particles, larger-size particles, large suspended solids, and solids are used to describe the materials separated by the mechanical separation devices. These tend to be considered of solids content and includes larger size particles than the other materials, that is the liquids with small particles. The terms, such as liquids and fine suspended particles, small particles, small suspended solids, and liquids, are used to describe the materials separated by the mechanical separation devices. These tend to be considered liquids content and includes smaller size particles than the other materials, such as the solids described above.

The HS process 400 receives a process stream 402, which may be a slurry from a slurry tank prior to being cooked. The HS process 400 separates the components, and further washes the material. The HF process 400 sends the process stream 402 through a first mechanical separation device 404, which separates components such as the larger solid particles from the smaller particles and liquids stream a first time. This is also referred to as a first pass. The first tank 410 may contain about 18% solids content(average).

The first mechanical separation device 404 may include paddles that rotate, a stationary drum, and an outer wall configured as a screen. The first mechanical separation device 404 pushes the process stream 402 against a screen where the liquids and small particles (i.e., starch, gluten, protein, salt, and the like) pass through the screen and are sent to a water makeup process 409, which makes the process stream 402 (as shown by the dotted line). The paddles rotate to move the process stream 402 toward the screen. The screen has openings that are sized to allow water, starch, and smaller sized particles to flow through the screen but will not allow the larger particles, such as fiber to flow through.

The HS process 400 produces a liquids and fine suspended particles stream 406 and a large suspended solids stream 408. The liquids and fine suspended particles stream 406 may include starch that has been washed and removed from the fiber. However, the large suspended solids stream 408 may still contain starch and/or the food grade protein. Thus, the HS process 400 may wash the fiber through a series of mechanical separation devices. For instance, embodiments of the HS process 400 may include but is not limited to, one, two, three, four, or up to about ten stages of washing and separation. In an embodiment, there may be one mechanical separation device to separate the large suspended solids stream from the liquids and fine suspended particles. In other embodiments, there may be two or more mechanical separation devices, up to ten mechanical separation devices. In FIG. 4, an embodiment of the HS process 400 illustrates four mechanical separation devices.

The HS process 400 directs the liquids and fine suspended particles stream 406 to a liquefaction tank 409 and sends the large suspended solids stream 408 to a first tank 410. The first tank 410 receives another liquids and fine suspended particles stream 422 from a third mechanical separation device 420. Here, the combined streams are mixed and heated to about 76° C. to about 85° C. (170° F. to about 185° F., about 349 K to about 358 K) for about 1 to about 60 minutes. In an embodiment, the combined streams are mixed and heated to about 82° C. (about 180° F., about 355 K) for about 5 minutes. The HS process 400 sends this combined stream from the first tank 410 to a second mechanical separation device 412.

The second mechanical separation device 412 washes and removes the starch from the fiber, producing another liquids and fine suspended particles stream 414 to be sent to a water makeup process 409, which makes the process stream 402 (as shown by the dotted line), or alternatively, to liquefaction tank, to makeup water for slurry tank, and another large suspended solids stream 416 to be sent to the second tank 418. The HS process 400 sends the combined stream from the first tank 410 through the second mechanical separation device 412, which separates components such as the larger solid particles from the smaller particles and liquids stream a secondtime, or referred to as a second pass. The second tank 418 may contain about 10% solids content (average). The second tank 418 receives yet another liquids and fine suspended particles stream 432 from a fourth mechanical separation device 430. Here, the combined streams are mixed and heated to about 76° C. to about 85° C. (170° F. to about 185° F., about 349 K to about 358 K) for about 1 to about 60 minutes. In an embodiment, the combined streams are mixed and heated to about 82° C. (about 180° F., about 358 K) for about 5 minutes. The HS process 400 further sends this combined stream from the second tank 418 to a third mechanical separation device 420.

The third mechanical separation device 420 removes starch left on the fiber, producing another liquids and fine suspended particles stream 422 to be sent to the first tank 410 and another large suspended solids stream 424 to be sent to a third tank 426. The HS process 400 sends the combined stream from the second tank 418 through the third mechanical separation device 420, which separates components such as the larger solid particles from the smaller particles and liquids stream a third time, or referred to as a third pass. The third tank 426 may contain about 7% solids content (average). Also, the third tank 426 receives cook water 428 and liquids stream 438 from a fourth mechanical separation device 430. The cook water 428 being added to the large suspended stream 424 may create a lower-solids stream in the third tank 426. The cook water 428 may include but is not limited to hot dilution water. The cook water 428 may range from a temperature of about 75° C. to about 99° C. In another embodiment, cook water is added to the second tank 418 and to the third tank 426. Here, the combined streams are mixed and heated to about 76° C. to about 85° C. (170° F. to about 185° F., about 349 K to about 358 K) for about 1 to about 60 minutes. In an embodiment, the combined streams are mixed and heated to about 82° C. (180° F., about 358 K) for about 2 minutes.

The HS process 400 sends the combined stream from the third tank 426 to the fourth mechanical separation device 430. The fourth mechanical separation device 430 produces the liquids and fine suspended particles stream 432 to be sent to the second tank 418 and the large suspended solids stream 434 to be sent through a device 436. This device 436 may be a dewatering device to create a liquids stream 438 and insolubles 440. The HS process 400 uses the device 436 to send the liquid stream 438 to the third tank 426. In embodiments, the HS process 400 sends the insolubles 440 to a dryer, sends the insolubles 440 to be sold as a wet product for livestock feed, and the like. The device 436 removes moisture from this portion of the large suspended solids stream 434, which is now about 64% moisture. In an embodiment, the material may be packaged as middlings. The middlings may be used as filler in pet food and/or for manufacturing semolina. Semolina is used to make breakfast cereals, puddings, pasta, and couscous for human food.

The device 436 may include, but is not limited to a screw press, a centrifuge, a rotary press, a rotary thickener, a filter belt, a vetter press, a belt press, a paddle screen, a vertical centrifuge, a washing centrifuge, a medium pressure screen, and the like. The device 436 separates any remaining insolubles 440 from the liquids 438.

The mechanical separation devices include at least one of a paddle machine, a paddle screen, a washing paddle machine, a filtration centrifuge, a pressure DSM screen, a SWACO screen, a medium pressure screen, a multi-zoned screening apparatus, a boxed screen, a gravity DSM screen, and the like. The multi-zoned screening apparatus described in Application No. PCT/US2013/054695 with Scott Kohl as an inventor is incorporated herein in its entirety. The mechanical separation devices use dilution of water, which is aqueous extraction of soluble materials from insoluble materials. Furthermore, the mechanical separation devices use a multi-stage washing of displacement washing, which uses the water more efficiently by using water from a stage of washing (i.e., pass) to another stage of washing (i.e, another pass).

In an embodiment, the mechanical separation device is the multi-zoned screening apparatus which includes a first and a second zone, a plurality of openings in the cylindrical screen in the zones, where a first section includes ribbon flight winding about vanes, and a plurality of paddles in a second section. In another embodiment, the first mechanical separation device is a paddle machine separation device having at least four rotating paddles with a stationary drum and an outer wall configured as a screen. In other embodiments, the paddle machine separation device may include at least two rotating paddles up to 20 rotating paddles.

The washing paddle machine may include multiple zones of washing within the paddle machine. For instance, there may be a two zone washing in the first mechanical separation device in an embodiment. However, any number of zone washings may be used, such as two, three, or four washing zones. The washing of the fiber or large solids helps to wash the starch and gluten or protein away from the fiber.

The first tank 410, the second tank 418, and the third tank 426 may be a cook tank or any type of tank that is agitated. Agitation can be performed with a mechanical agitator or with an external pump recirculating back to the tank. The residence time in the tanks may be predetermined based on variables. The variables may include size of the tank, amount of material, type of grain, and the like.

The cooking of the large suspended solids stream with the water causes the starch granules to absorb the water as heated. Thus, water is absorbed inside the granule. This swelling of the granule allows for improved enzyme action when returned to the start of the slurry process.

In an embodiment, the mechanical separation devices 404, 412, 420, 430 may each be a paddle machine separation device having at least four rotating paddles with a stationary drum and an outer wall configured as a screen. In other embodiments, the paddle machine separation device may include but is not limited to at least two rotating paddles up to 20 rotating paddles.

In an embodiment, the mechanical separation devices 404, 412, 420, and 430 may be the same type of separation devices. In other embodiments, the mechanical separation devices 404, 412, 420, and 430 may each be different types of separation devices, or a combination of similar and different types of devices. For instance, in an embodiment, the first mechanical separation device 404 may be a paddle machine separation device with two zones of washing and the second mechanical separation device 412 may be a paddle machine separation device with a single zone of washing.

The size of the screens to be used may be based on micron sizes, which are spaces between the wires in the screens. Embodiments in the HS process may use micron sizes of 75, 100, 150, 250, and the like. The screen sizes are determined based on the desired size of the large-size particles to be separated from the liquids and small particles. The desired particles to be screened may range from 100 to 300 micro meters.

In embodiments, the HS process sends the water streams containing fine suspended solids and dissolved solids to the slurry mix tank to be blended as slurry, to be sent to be cooked with or without a jet cooker, to be sent to the liquefaction tank, or sent to the fermentation tank to be fermented.

Figure 5:
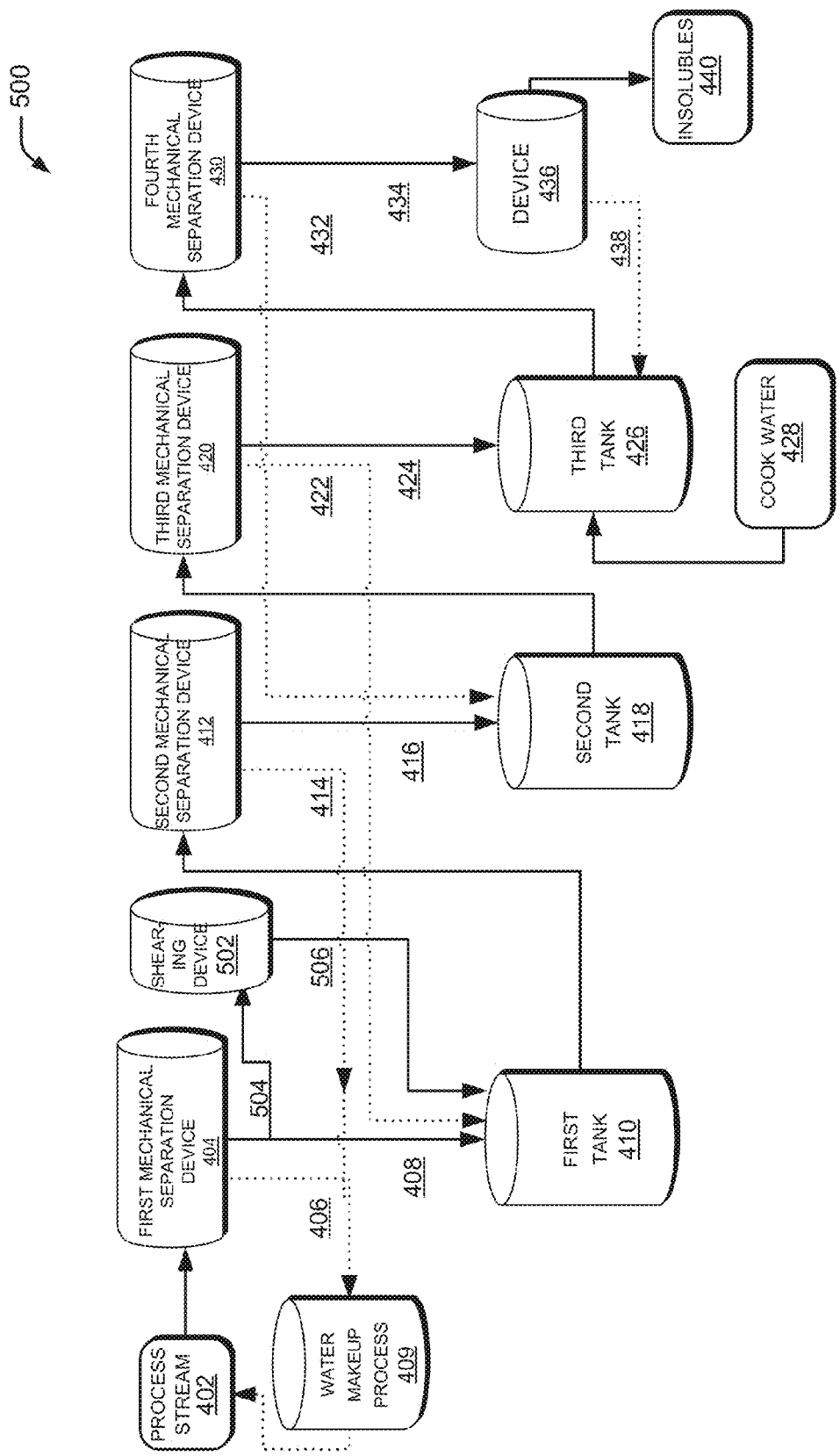
FIG. 5 illustrates another example of a hybrid separation process using the counter-flow wash process with a shearing device.

FIG. 5 illustrates another example of the HS process 500 using a counter-flow wash process. FIG. 5 is similar to FIG. 4, except for the addition of a shearing device 502. The HS process 500 sends the process stream 402 through the first mechanical separation device 404. The HS process 500 produces a liquids and fine suspended particles stream 406 and a large suspended solids stream 408. The HS process 500 sends the liquids and fine suspended particles stream 406 to the liquefaction tank 409. However, the large suspended solids stream 408 may still contain starch and/or the food grade protein. Thus, the HS process 500 may shear and wash the starch from the fiber through a shearing device 502 combined with a series of mechanical separation devices. Any type of shearing device may be used. For instance, the HS process 500 may include a shearing device 502 that provides different amounts of shear . . . . Shearing device include, but is not limited to, impact mill, disc mill, roller mill, centrifugal pump, ventri jet, hydroheater, pin mill, and the like.

The HS process 500 sends the large suspended solids stream 408 to a first tank 410. A portion or all 504 of this stream 408 is directed towards the shearing device 502. This portion 504 of the large suspended solids stream 408 is further sheared by the shearing device 502. Then the process 500 sends the ground materials 506 from the shearing device 502 to the first tank 410.

The first tank 410 receives another liquids and fine suspended particles stream 422 from a third mechanical separation device 420. Here, the combined streams are mixed and heated to about 76° C. to about 85° C. (170° F. to about 185° F., about 349 K to about 338 K) for about 1 to about 60 minutes. In an embodiment, the combined streams are mixed and heated to about 82° C. (180° F., about 355 K) for about 5 minutes. The process 500 sends this combined stream from the first tank 410 to a second mechanical separation device 412. The rest of the process 500 from this point is similar to the HS process 400 described with reference to FIG. 4.

An embodiment includes incorporating shearing step after each mechanical separation step. For instance, a first shearing device is placed after the first mechanical separation step, and a second shearing step is placed after the second mechanical separation step. In other embodiments, there could be three, four, or five shearing steps placed after each of the three, four, or five mechanical separation steps, respectively. For instance, there may be four mechanical separation steps and there are four shearing steps placed after each of the mechanical separation steps.

In other embodiments, there may be less shearing steps than there are mechanical separation steps. For instance, there may be a first shearing step after a first mechanical separation step, and additional mechanical separation steps without any shearing devices after each of them. In other embodiments, a single shearing step may be placed after any mechanical separation steps, other than the first mechanical separation step. For instance, a single shearing step may be placed after the second mechanical separation step, the third mechanical step, the fourth mechanical separation step, and the like.

In other embodiments, two shearing steps may be placed after two mechanical separation steps. For instance, a first shearing step may be placed after a first mechanical separation step device and a second shearing step placed after a third mechanical separation step. In other embodiments, the shearing steps may be placed after a first and a second mechanical separation steps with more mechanical separation steps that do not have shearing devices associated with them. Any combinations of shearing steps and mechanical separation steps to shear and to separate materials, are to be understood by the person of having ordinary skill in the art.

Figure 6:
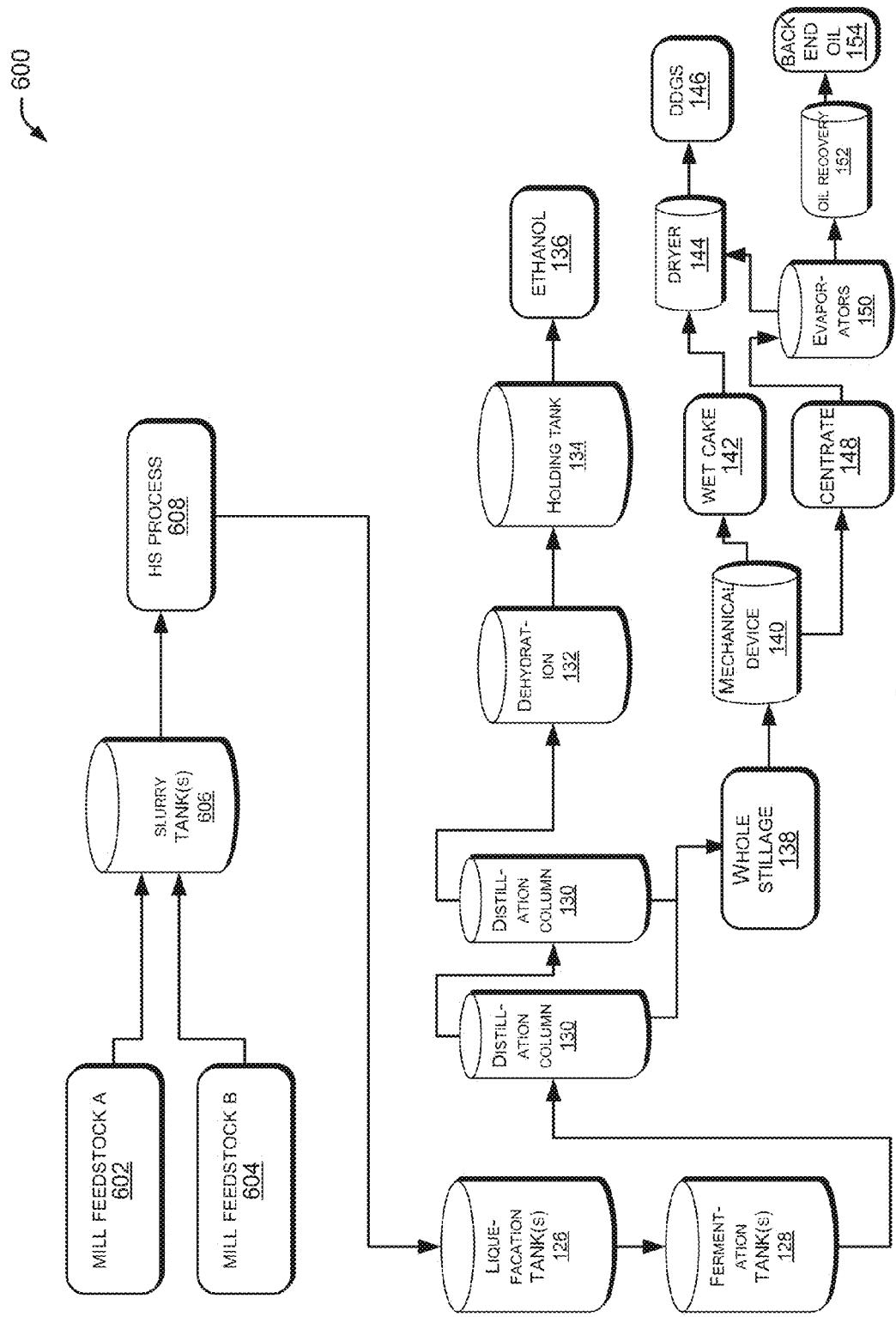
FIG. 6 illustrates an example environment for implementing the hybrid separation process with a combined feedstock of different types of grain.

FIG. 6 illustrates an example environment 600 for implementing the HS process with a combined feedstock. FIG. 6 illustrates a milling process for feedstock A 602, a milling process for feedstock B, and creating a slurry with both feedstocks and adding enzymes to a slurry tank 606. In another embodiment, the environment 600 may include other feedstocks, such as C or D. The process 600 sends the process stream from the slurry tank 606 to the HS process 608 The HS process 608 has been described with reference to FIG. 4, with reference to FIG. 5 or any of the embodiments. After the HS process 668, the process may have similar functions and equipment as the process described with reference to FIG. 1.

Figure 7:
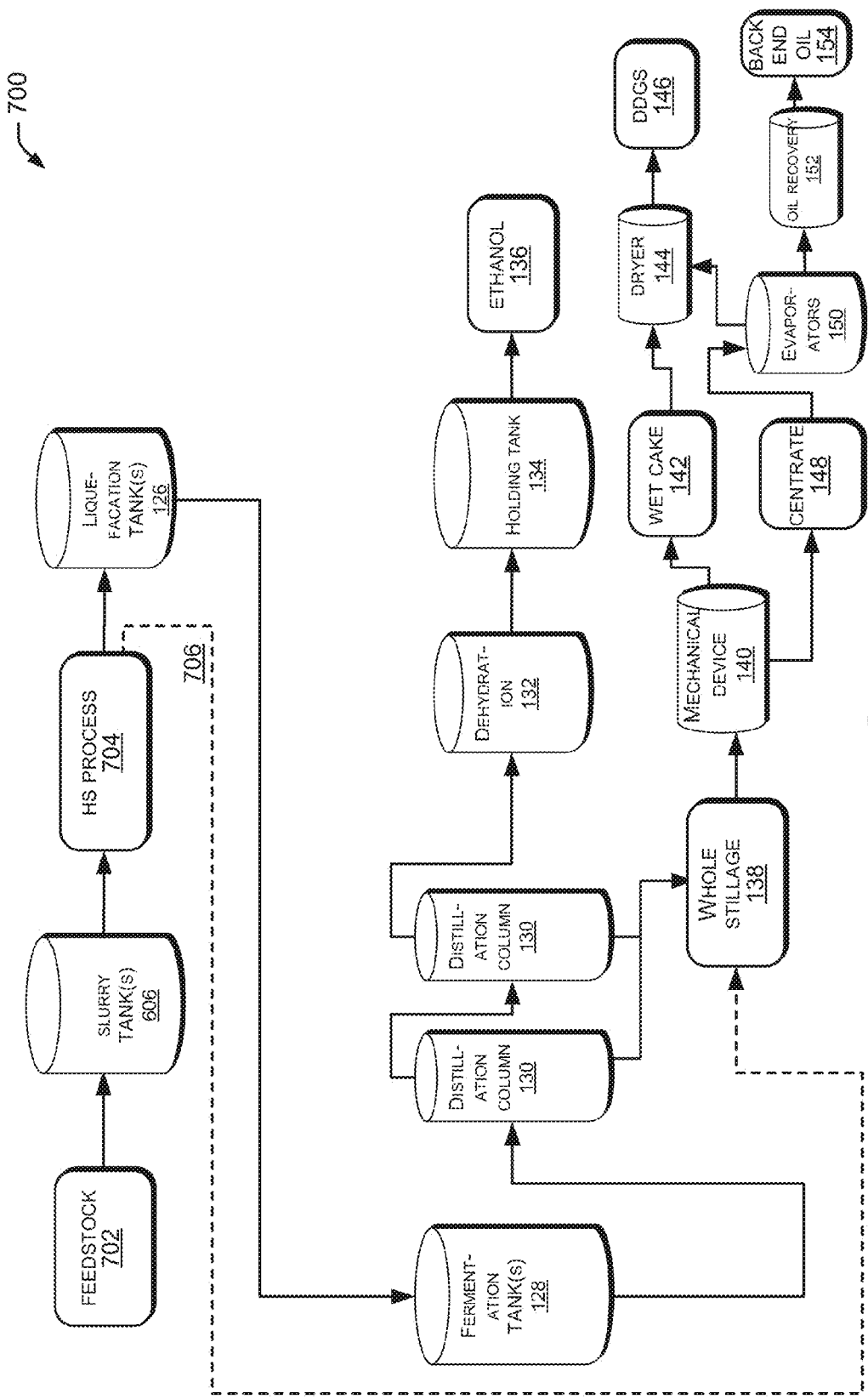
FIG. 7 illustrates another example environment for implementing the hybrid separation process with a single feedstock of grain.

FIG. 7 illustrates an example environment 700 for implementing the HS process with a single feedstock 702. The process 700 illustrates combining feedstock 702 with a slurry and adding enzymes to a slurry tank 606. The process 700 sends the process stream from the slurry tank 606 to the HS process 704. The HS process 704 has been described with reference to FIG. 4, with reference to FIG. 5, or any of the embodiments. Here, the process 700 may send materials 706 shown in a dotted line, from the HS process 704 directly as whole stillage 138. The materials 706 bypass fermentation and distillation processes to be used as wet cake for livestock feed. This is possible because clean water in the same form as process makeup water today is added later in the cook process of the production facility and used as a counter-flow washing system. Thus, this moves all of the solubles toward the front of cook and leaves the cleaned solids to be separated and bypasses around fermentation to whole stillage tank prior to existing the mechanical device.

After the HS process 704, the process may have similar functions and equipment as the process described with reference to FIG. 1.

Examples of Enzymes

Figure 8:
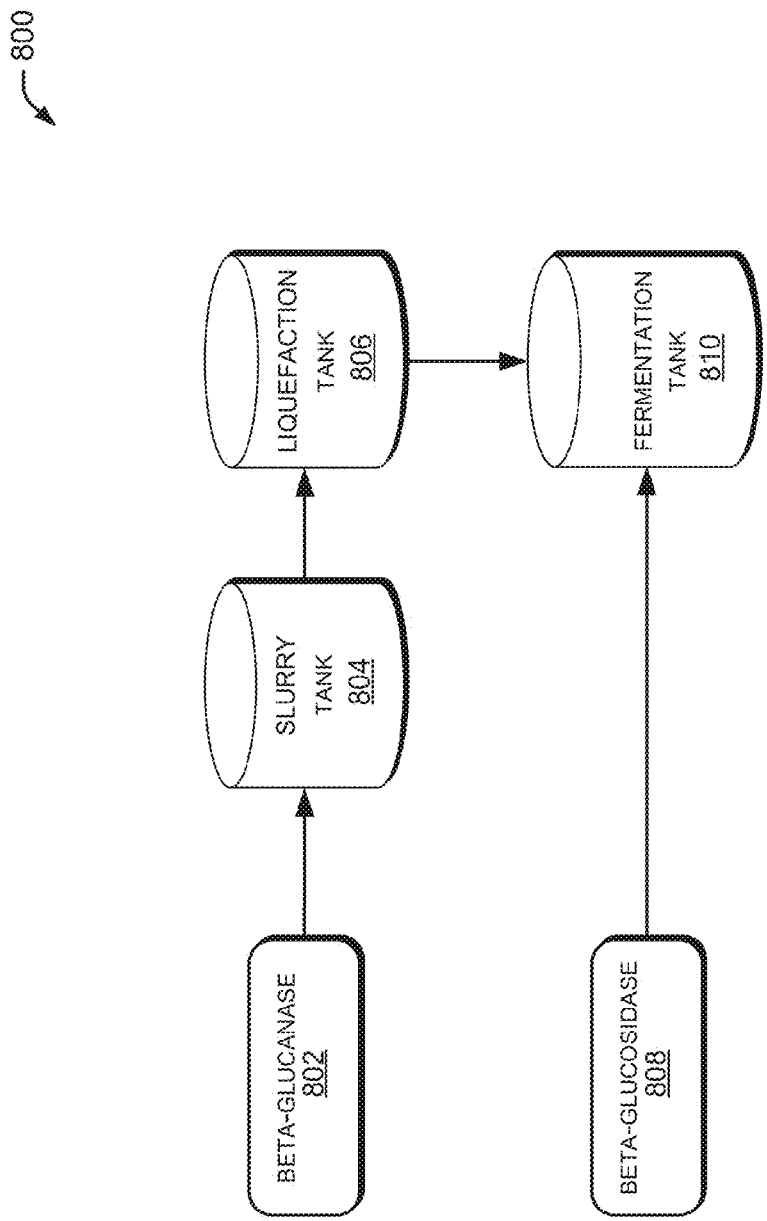
FIG. 8 illustrates an example of adding enzymes to the production process.
Figure 9:
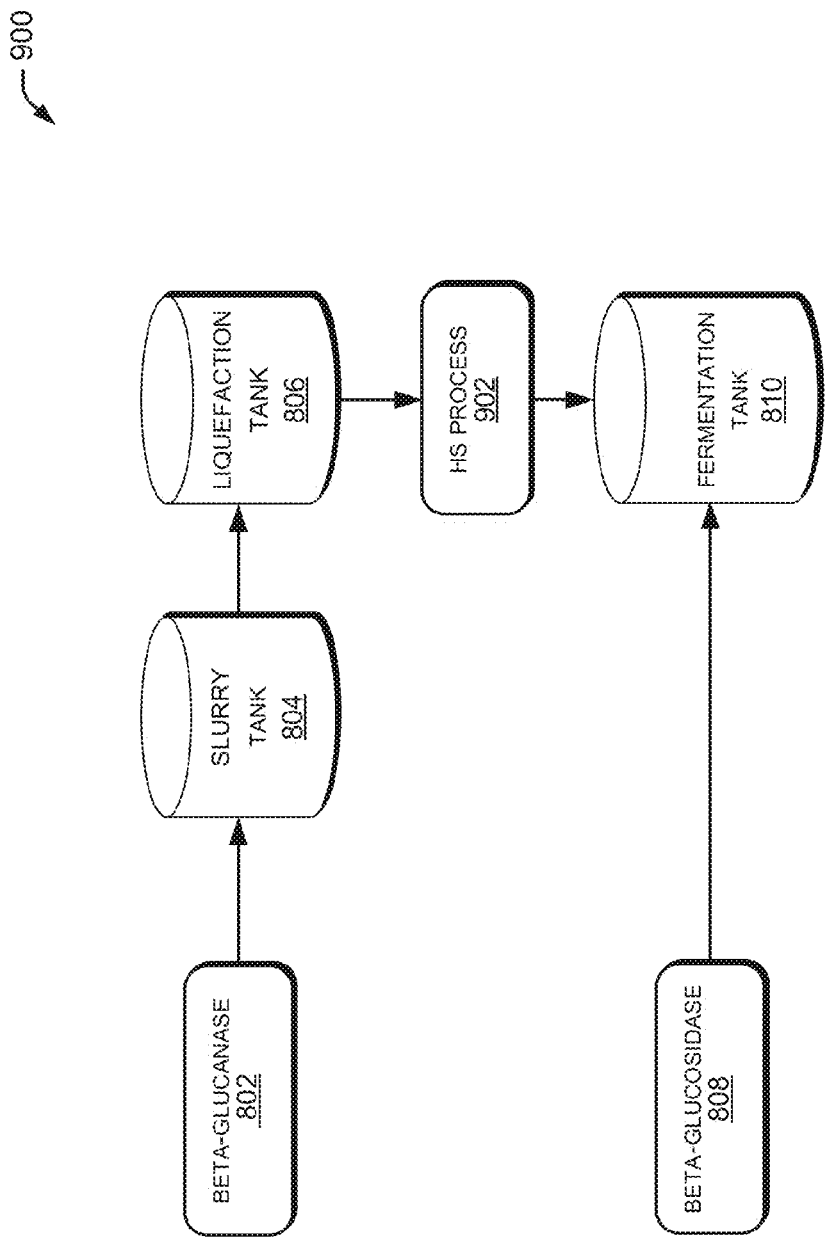
FIG. 9 illustrates another example process of adding enzymes to the production process in combination with the HS process.
Figure 10:
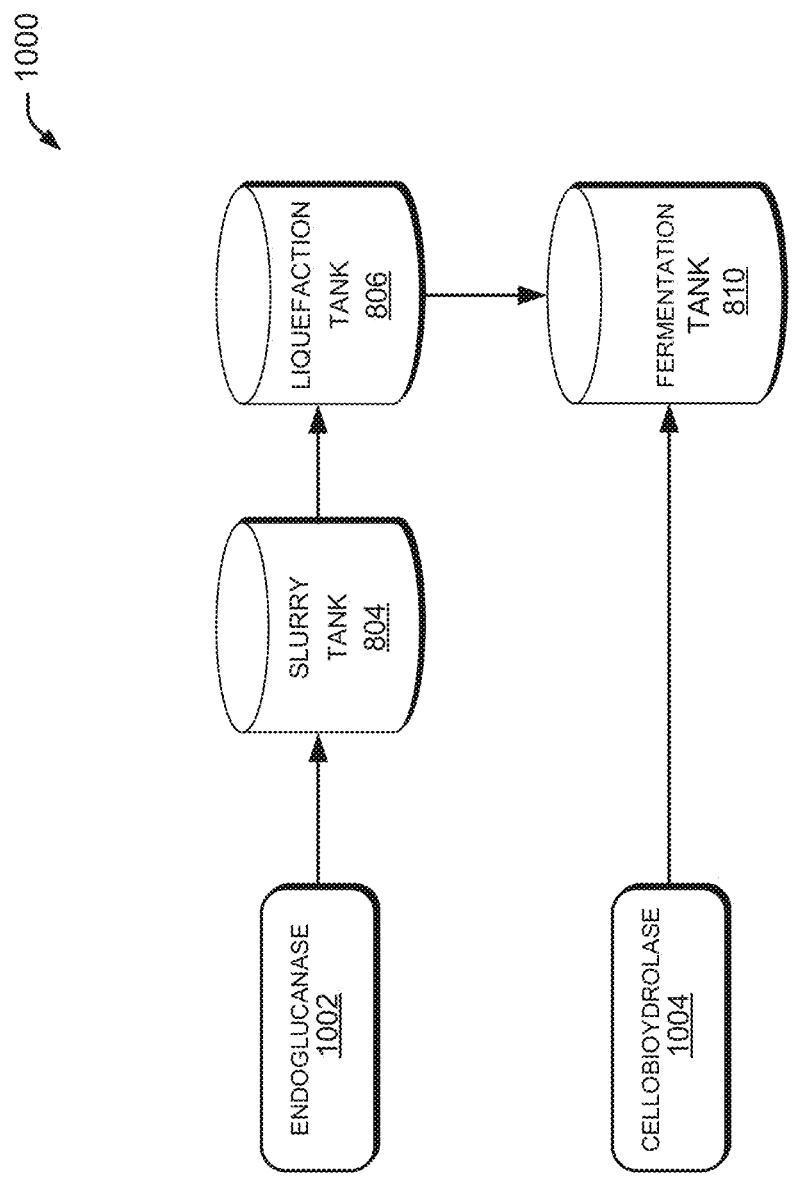
FIG. 10 illustrates another example of adding other types of enzymes to the production process.

FIGS. 8-10 illustrate examples of adding enzymes to a production process. The enzymes may be combined in any amount, any order or any matter. For instance, the enzymes described with reference to FIGS. 8 and 9 can be combined with the enzymes described with reference to FIG. 10.

FIG. 8 illustrates an example process 800 of adding enzymes to a production process. The feedstock may include any type of grains. This process 800 adds water and enzymes, beta-glucanase 802 to combined materials to create a slurry in a slurry tank 804. In an example, enzymes that may be added include, but are not limited to, alpha-amylase and beta-glucanase 802. The alpha-amylase breaks starch polymer into short sections. The amount of alpha-amylase may range from 0.02 to 0.06 w/w % of incoming grain (depending on activity in enzyme formulation) added at about 65° C. (about 150° F.). Meanwhile, the beta-glucanase 802 breaks down beta-linked glucose polymers that are associated with grains. The beta-glucanase 802 breaks down glucan, a polysaccharide made of several glucose sub-units. The glucan break down may occur randomly of the molecule. Beta-glucanase 802 that may be used include, but is not limited to, β-1,3-glucanase, an enzyme that breaks down β-1,3-glucans and β-1,6-glucanase, an enzyme that breaks down β-1,6-glucans. The amount of beta-glucanase 802 may range from 0.005 to 0.06 w/w % of incoming grain (depending on activity in enzyme formulation).

Beta-glucanase 802 has been found to be particularly effective with the grains of barley, as it attacks β-glucan fiber to liberate smaller fragments (i.e., a cell wall modification). The rate of modification is determined by contents of the cell walls of beta-glucan. Beta-glucanase 802 hydrolyzes beta D-glucan component and breaks down the beta-linked glucose polymers that are often associated with barley or wheat.

The pH of the slurry may be adjusted to about 5.0 to 6.0 in the slurry tank 804. Furthermore, the temperature may be maintained between 60 to 150° C. (333 to 423 K) in the slurry tank 804 and a residence time of about 30 to 120 minutes to convert the insoluble starch in the slurry to soluble starch. The slurry may have dissolved solids content of about 18 to 44%. Other items in the slurry tank 804 may include sugars, protein, fiber, starch, germ, grit, oil and salts, and the like. There may be one or more slurry tanks in the production facility.

In embodiments, the slurry may or may not be heated in the slurry tank to reduce viscosity of the milled grain. Some processes may include an optional jet cooking process. When the jet cooking process is used, jet cookers (not shown) will cook the slurry. Jet cooking may occur at elevated temperatures and pressures. For example, jet cooking may be performed at a temperature of about 100 to 150° C. (about 212 to 302° F., about 373 to about 423 K) and at an absolute pressure of about 100 to 6.0 kg/cm$^2$ (about 15 to 85 lbs/in$^2$) for about five minutes. Jet cooking is one method used to gelatinize the starch.

The process 800 converts the slurry to mash in a liquefaction tank 806. This occurs at about 80 to 95° C. (about 353 to 368 K) to hydrolyze the gelatinized starch into maltodextrins and oligosaccharides to produce a liquefied mash. Here, the mash stream has about 18 to 40% total solids content. The mash may have suspended solids content that includes fiber, germ, grit, and the like.

The process 800 adds microorganism, amyloglucosidase, and another enyzme, beta-glucosidase 808 to the mash in a fermentation tank 810. A common strain of microorganism, such as *Saccharomyces cerevisiae* may be used to convert the simple sugars (i.e., maltose and glucose) into alcohol (with solids and liquids), $CO_2$, and heat.

The beta-glucosidase 808 is a glucosidase enzyme that acts upon β-1-3, β-1-4 bonds that link two glucose molecules or glucose-substituted molecules. By cleaving the β-1-3, β-1-4 linkage, beta-glucosidase 808 may generate D-glucose. In other words, the beta-glucosidase 808 acts on these molecules by releasing a sugar molecule. In particular, the beta-glucosidase 808 has specificity for a variety of beta-D-glycoside substrates. The process 800 adds the beta-glucosidase 808 at about 40° C. to about 28° C. (about 313 to 301 K) and in a range from 0.001 to 0.09 w/w % of incoming grain.

The combination of beta-glucanase 802 and beta-glucosidase 808 is able to ferment the components of barley. For instance, barley contains about 56% starch and 4% betaglucan. These two enzymes work together to help make beta-glucan appear more like glucose to yeast. Thus, the effective, fermentable concentration has been taken to be about 60%. Therefore, the yield increases by 12%, lowering a need from 47.7 million bushels of barley per year to 41.2 million bushels of barley per year and the amount of wheat bushels needed from 14.7 million bushels per year to 15.2 million bushels per year for a 115 denatured alcohol MMgpy production facility.

FIG. 9 illustrates another example process 900 of adding the beta-glucanase 802 and beta-glucosidase 808 enzymes to the production process in combination with a HS process 902. The HS process 902 may be the HS process described with reference to FIG. 4, with reference to FIG. 5, or with any of the embodiments described above.

FIG. 10 illustrates another example process 1000 of adding other enzymes to the production process. The feedstock may include any type of grains. This process 1000 is similar to the process described with reference to FIG. 8. This process 1000 adds water and enzymes to combined materials to create a slurry in a slurry tank 804. In an example, enzymes that may be added include but are not limited to, alpha-amylase and endoglucanase 1002. The endoglucanase 1002 catalyzes the hydroloysis of cellulose. The endoglucanase 1002 cleaves internal bonds of the cellulose chain. Other enzymes may be further used to further break down the cellulose chain. These enzymes include but are not limited to exoglucanases and beta-glucosidases. The amount of endoglucanase 1002 varies depending on the dosage amount, type of materials, and the like.

The process 1000 further adds microorganism and another enyzme, cellobioydrolase 1004 to the mash in a fermentation tank 810. A common strain of microorganism, such as *Saccharomyces cerevisiae* may be used to convert the simple sugars (i.e., maltose and glucose) into alcohol (with solids and liquids), $CO_2$, and heat.

The cellobioydrolase 1004 hydrolyzes cellulose to glucose. The process 1000 may add the cellobioydrolase 1004 at 45° C. to about 75° C. (about 313 to 349 K), 78° C. to 99° C. about 351 to 372 K), or 100 to 150° C. (373 to 423 K) and in a range from 0.005 to 0.06 w/w % of incoming grain.

Those of ordinary skill in the art will recognize how to modify existing alcohol processes or other type of processes to include the HS process, and/or to add the enzymes to increase alcohol yield.

Examples of Test Results

Figure 11:
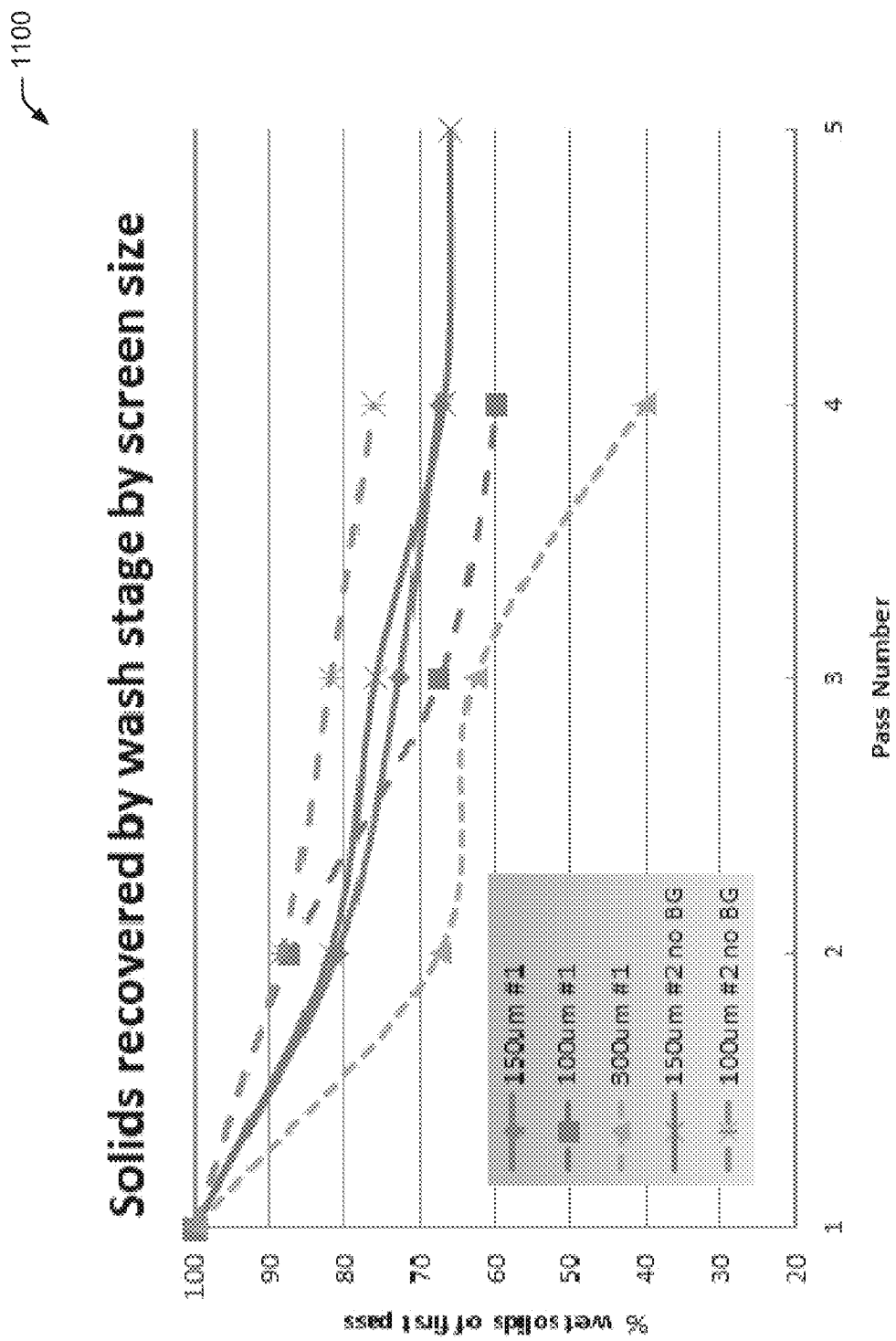
FIG. 11 illustrates an example of test results of the hybrid separation process using the counter-flow wash process.

FIG. 11 illustrates an example graph 1100 of test results using the HS process described with reference to FIG. 4, with reference to FIG. 5 or any of the embodiments described above. The graph 1100 represents the solids that are recovered by a number of passes through the mechanical separation devices based on screen sizes.

The data in the graph 1100 is from a study that evaluated the process of washing starch from the fiber by using the HS process. The study used different size screens for the paddle machine and various number of passes. For instance, the screen sizes have screen openings of 100 µm, 150 µm, and 300 µm.

Turning to the graph 1100, a y-axis shows the "% Wet Solids" measured from the samples after going through a mechanical separation device. The x-axis shows the "Number of Passes" for the streams in the samples that passed through one mechanical separation device up to five mechanical separation devices.

The graph 1100 illustrates the efficiencies of each pass. For instance, each pass may lose additional material through the screen. The mechanical separation devices were able to remove starch each time.

In another study, HS process was replicated in a pilot plant using the HS embodiments described above. Table I. illustrates results of Oil Recovery based on gallons per minute run in the pilot plant, as shown in the second column and samples of Control (no hybrid separation) and Hybrid Separation, as shown in the first column.

TABLE I

| Oil Recovery | |
|---|---|
| Samples | Oil Recovery |
| Control | 2.47 gpm |
| Hybrid Separation with shearing device | 3.43 gpm |

Table I. illustrates there is an increase of about 39% in recovering oil implementing the HS process, as described with reference to FIG. 5 or one of the embodiments incorporating a shearing device.

Table II. illustrates benefits observed during the pilot plant run.

| Row | Measurement | Control | HS Process | Difference |
|---|---|---|---|---|
| 1 | Temperature to beer column | 135.9° F. | 141.5° F. | 5.6° F. |
| 2 | Pressure across exchangers | 76.7 psi | 45.1 psi | −31.6 psi |
| 3 | Avg. HPLC beer | 12.27 w/v % | 12.52 w/v % | 2.0 w/v % |
| 4 | Gallons 200 proof | 71,236 | 78,809 | 10.6% |
| 5 | Gallons liquefaction per gallon 200 proof | 7.84 | 7.15 | −8.80 |
| 6 | Gallons beer per gallon 200 proof | 7.04 | 6.58 | −6.53 |

Turning to Table II., in rows 1 and 2, the HS process helps increase the temperature in the beer column and reduce the pressure across heat exchangers, which reduce the amount of energy used for downstream processing. In rows 5-6, the amount of gallons of liquefaction and beer needed to produce 200 proof has been reduced. Thus, the HS process provides benefits and help operate the plant more efficiently.

In another study, Tables III. and IV. below illustrate the ethanol yield observed from a laboratory. The yield is measured in two methods, HPLC at end of experiment (shown as Table III.) as well as weight loss with mostly sealed container (shown as Table IV.). The HPLC or weight loss numbers are then related back to the dry solids content of the mash for each test. The relationship provides a ratio of ethanol to dry solids and the control sample value is used to judge the effect of the treatment conditions. There are two "controls" reported in the weight loss data due to stress on yeast.

The first control is comparing all the mashes to the LLF L2 Mash. The second control is comparing all the mashes to the Low Density L2 Mash. The Low Density L2 Mash had tap water added to the LLF L2 Mash material with the goal having the same solids as the HS treated samples. The control samples were taken post liquefaction. Secondary controls were diluted with water to match the dilution artifact of the HS lab simulation.

Experimental samples were taken from earlier in the cook process. These samples were treated to predict the performance of the HS process. A blender was used as a surrogate for the shearing device in the full-scale operation. This method has been used in the past of shearing and predicts performance fairly well. Solids retained on a mechanical separation device were mixed with an equal mass of water (1000 g wet solids were mixed with 1000 g tap water). This mixture was treated by different processes:

1) increase to 85° C. (358 K) for a few minutes,
2) increase to 85° C. (358 K) for four hours,
3) increase to 85° C. (358 K), shear for 30 seconds with blender and hold at 85° C. (358 K) for four hours,
4) increase to 85° C. (358 K), shear for 120 seconds with blender and hold at 85° C. (358 K) for four hours,
5) increase to 85° C. (358 K), shear for 120 seconds with blender, increase to 95° C. (368 K) and hold for four hours, and
6) increase to 85° C. (358 K), shear for 120 seconds with blender, increase to 130° C. (403 K) for 30 minutes, then hold at 85° C. (358 K) for four hours.

After treatments, solids from the mechanical separation device were recombined with the treated solids such that 700 g of treated solids were mixed with 1400 g of solids. Treated liquefaction was then processed through the fermentation process described below. This process dilutes the mash and will impact fermentation with lower final ethanol concentration. In order to try to account for this post liquefaction, mash was diluted to the same % dry solids (DS as measured by plant) as the treated mashes and processed with the other treatments. This "secondary control" method was used to better interpret the effect of the treatments and isolate the treatments from the dilution affect.

The mashes were prepared for fermentation by adding mash solids, enzymes, urea, and antibiotic. The mashes were then dry pitched with active dry yeast. The mashes were stirred for about 10 minutes, and then triplicate flasks were prepared by adding 150 gm of mash to 250 ml Erlenmeyer flasks. The flasks were sealed with a rubber stopper containing an 18 gauge needle to vent the flask and then placed in temperature control rotary shaker set at 150 rpm and 32° C. At approximately 6, 24, 48 and 70 hours, samples were removed from the flasks for HPLC analysis. Another set of fermentors were prepared in triplicate to follow the fermentation by weight loss by adding 150 gm of mash to tarred 250 ml Erlenmeyer flask. The flasks were sealed with a rubber stopper containing an 18 gauge needle and placed in the temperature controlled shaker at the conditions described above. When the flasks were sampled for HPLC analysis, the weight loss flasks were weighed. The weight loss was then used to calculate the amount of ethanol produced.

After 70 hours of fermentation, the beer in the weight loss flasks was transferred to a tarred plastic weigh boat and dried at 65° C. (338 K) to obtain DDGS. The weight of the DDGS was noted and used to calculate the yield of DDGS. The DDGS samples were assayed for moisture, starch, protein and oil.

Table III. illustrate ethanol yield by HPLC and Table IV. illustrate ethanol yield by weight loss.

TABLE III

Ethanol yield by HPLC

| Treatment | g/L Ethanol in beer by HPLC | EtOH conc/ dry solids | HPLC delta to control (%) | delta to Low Density L2 Mash | dry solids in sample |
|---|---|---|---|---|---|
| LLF L2 Mash | 125.7 | 3.96 | 100.0 | 97.8 | 31.7 |
| Low Density L2 Mash | 99.7 | 4.05 | 102.2 | 100.0 | 24.6 |
| No shear 4 hr cook | 101.4 | 4.19 | 105.8 | 103.5 | 24.2 |
| Short shear 4 hr cook | 92.4 | 4.07 | 102.8 | 100.6 | 22.7 |
| Long shear 4 hr cook | 102.1 | 4.14 | 104.5 | 102.2 | 24.7 |
| Long shear + jet + 4 hr cook | 101.6 | 4.12 | 104.1 | 101.9 | 24.6 |
| Long shear + 95 C 4 hr cook | 102.2 | 4.13 | 104.2 | 102.0 | 24.8 |

Note solids content per sample type

TABLE IV

Ethanol yield by weight loss

| Treatment | weight loss g/g solids in mash | weight loss delta to control (%) | weight loss delta to Low Density L2 Mash | dry solids in sample |
|---|---|---|---|---|
| LLF L2 Mash | 10.9 | 100.0 | 97.3 | 31.7 |
| Low Density L2 Mash | 11.2 | 102.7 | 100.0 | 24.6 |
| No shear 4 hr cook | 11.9 | 108.7 | 105.8 | 24.2 |
| Short shear 4 hr cook | 11.3 | 103.5 | 100.8 | 22.7 |
| Long shear 4 hr cook | 11.6 | 106.3 | 103.4 | 24.7 |
| Long shear + jet + 4 hr cook | 11.7 | 106.8 | 103.9 | 24.6 |
| Long shear + 95 C 4 hr cook | 11.7 | 107.1 | 104.3 | 24.8 |

Note solids content per sample type

Tables III. and IV. illustrate that lowering the solids of mash even just immediately before fermentation increases the ethanol yield. The Low Density L2 Mash showed 2.2% and 2.7% higher ethanol yields by HPLC and weight loss, respectively, compared to the LLF L2 Mash (full strength). Lowering mash density increases ethanol yield potential, but other studies showed that having lower mash solids during the cook process gave higher yields. This study lowered the mash solids after cook and had a similar result.

Tables III. and IV. illustrate that treating the more recalcitrant solids of cook with the HS process resulted in further increased ethanol yield. On average, the different treatments increased the observed ethanol yield by 2% and 3.6% measured by HPLC and weight loss, respectively, compared to the Low Density L2 Mash. (Comparing the different HS treatments to the full strength mash shows increased yield of 3.9% and 6.5%, HPLC and weight loss methods, respectively.

These examples represent include data, but are not limited to the laboratories and pilot plant studies that have been performed. These examples do not include data from all laboratories and pilot plant studies. These examples illustrate increasing ethanol yield that ranges from about 1% to about 3% and increasing oil recovery that ranges from about 10% to about 50%.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A separation method performed in a production facility to improve yield, the method comprising:
   filtering a first large-particles stream from a first liquid stream containing small particles of a process stream by using a first mechanical separation device in a counter-flow wash process in a series;
   adding water to the first large-particles stream in a tank to create a lower-solids stream;
   heating the lower-solids stream in the tank; and
   removing extra water from the lower-solids stream by using a second mechanical separation device in the counter-flow wash process that further separates a second large-particles stream from a second liquid stream containing small particles of the lower-solids stream;
   wherein the separation method is performed downstream of liquefaction and upstream of fermentation.

2. The method of claim 1, wherein the lower-solids stream in the tank is heated to a temperature lower than about 90° C. (about 363 K) to remove starch.

3. The method of claim 1, wherein the lower-solids stream in the tank is heated to a temperature higher than about 100° C. (about 373 K) to leach oil.

4. The method of claim 1, wherein the first or the second mechanical separation device comprises at least one of a multi-zoned screening apparatus, a paddle screen, a filtration centrifuge, or a pressure screen.

5. The method of claim 1, further comprising:
sending a portion of the first large-particles stream to a shearing device;
shearing particles in the portion of the first large-particles stream by using the shearing device; and
sending the particles sheared to be combined with the water and the first large-particles stream in the tank to create the lower-solids stream.

6. The method of claim 5, wherein the shearing the particles comprises using at least one of a disc mill, an impact mill, a roller mill, a centrifugal pump, a ventri jet, or a hydro-heater.

7. The method of claim 1, wherein the first mechanical separation device produces a solids content of about 18%.

8. The method of claim 1, further comprising causing an increase in ethanol yield ranging from about 1% to about 3%, by fermenting the second liquid stream containing small particles to produce ethanol.

9. The method of claim 1, further comprising recovering an increased amount of oil ranging from about 10% to about 50%, by sending the second liquid stream containing small particles through an oil recovery process to recover oil.

10. The method of claim 1, further comprising:
adding water to the second large-particles stream in another tank to create another lower-solids stream; and
heating the another lower-solids stream in the another tank.

11. The method of claim 10, further comprising:
filtering a third large-particles stream from a third liquid stream containing small particles of the process stream by using a third mechanical separation device; and
receiving the third large-particles stream to further separate insolubles from liquids in the third large-particles stream by using a dewatering device.

* * * * *